United States Patent
Smith

(10) Patent No.: US 6,940,600 B1
(45) Date of Patent: Sep. 6, 2005

(54) APPARATUS AND METHOD FOR MEASURING DECAY IN INTENSITY OF ELECTROMAGNETIC RADIATION IN MULTIPASS SPECTROMETRY

(75) Inventor: Alan Joseph Smith, Blackley (GB)

(73) Assignee: Shimadzu Research Laboratory (Europe) Ltd., Manchester (GB)

(*) Notice: Subject to any disclaimer, the term of this patent is extended or adjusted under 35 U.S.C. 154(b) by 0 days.

(21) Appl. No.: 10/030,317
(22) PCT Filed: Apr. 14, 2000
(86) PCT No.: PCT/GB00/01431
§ 371 (c)(1), (2), (4) Date: Oct. 19, 2001
(87) PCT Pub. No.: WO00/65328
PCT Pub. Date: Nov. 2, 2000

(30) Foreign Application Priority Data

Apr. 22, 1999 (GB) .............................. 9909319

(51) Int. Cl.$^7$ .............................. G01N 21/61
(52) U.S. Cl. .................... 356/437; 356/440
(58) Field of Search .............. 356/432, 437, 356/440, 246, 247; 250/343, 344, 345, 339.13

(56) References Cited

U.S. PATENT DOCUMENTS

| | | | |
|---|---|---|---|
| 4,322,621 A | 3/1982 | Aagard | |
| 5,220,402 A | 6/1993 | Harvey | |
| 5,222,389 A | * 6/1993 | Wong | ........................ 73/31.02 |
| 5,485,276 A | 1/1996 | Bien et al. | |
| 5,721,430 A | 2/1998 | Wong | |
| 5,742,054 A | 4/1998 | Atkinson | |
| 5,747,807 A | 5/1998 | Atkinson et al. | |
| 5,815,277 A | 9/1998 | Zare et al. | |
| 5,835,231 A | 11/1998 | Pipino | |
| 5,841,533 A | 11/1998 | Atkinson | |
| 5,854,684 A | 12/1998 | Stabile et al. | |
| 6,181,426 B1 | * 1/2001 | Bender et al. | ............... 356/432 |

FOREIGN PATENT DOCUMENTS

| | | |
|---|---|---|
| DE | 90 17 745.2 | 12/1990 |
| DE | 42 14 840 A1 | 5/1992 |
| JP | 55039049 | 3/1980 |
| JP | 05296934 | 11/1993 |
| WO | WO 93/13401 | 7/1993 |

OTHER PUBLICATIONS

Anderson et al., "Mirror reflectometer based on optical cavity decay time," *Applied Optics*, 23:1238–1244 (1984).
Herbelin et al., "Sensitive measurement of photon lifetime and true reflectances in an optical cavity by a phase–shift method," *Applied Optics*, 19:144–147 (1980).
Hodges et al., "Laser bandwidth effects in quantitative cavity ring–down spectroscopy," *Applied Optics*, 35:4112–4117 (1996).

(Continued)

Primary Examiner—Richard A. Rosenberger
(74) Attorney, Agent, or Firm—Leydig, Voit & Mayer, Ltd.

(57) ABSTRACT

An apparatus for measuring decay in intensity of electromagnetic radiation passing through a radiation-absorbent sample due to absorption of radiation by the sample is disclosed which includes a source of electromagnetic radiation having a wavelength within an absorption band of the sample and a plurality of partially-reflective specular surfaces which are spaced apart from each other along a predetermined path through the sample, each specular surface separating the incident radiation into a reflected part which follows the predetermined path and an unreflected part, the value of the decay being derived from intensity measurements of the unreflected parts made at different positions along the predetermined path.

22 Claims, 8 Drawing Sheets

OTHER PUBLICATIONS

Jongma et al., "Trace gas detection with cavity ring down spectroscopy," *Rev. Sci. Instrum.*, *68*:2821–2828 (1995).

O'Keefe and Deacon, "Cavity ring–down optical spectrometer for absorption measurements using pulsed laser sources," *Rev. Sci. Instrum.*, *59*:2544–2551 (1988).

Scherer et al., "Cavity Ringdown Laser Absorption Spectroscope: History, Development, and Application to Pulsed Molecular Beams," *Chem. Rev.*, *97*:25–51 (1997).

White, "Long Optical Paths of Large Aperture," *J.O.S.A.*, *32*:285–288 (1942).

Zalicki and Zare, "Cavity ring–down spectroscopy for quantitative absorption measurements," *J. Chem. Phys.*, *102*:2708–2717 (1995).

\* cited by examiner

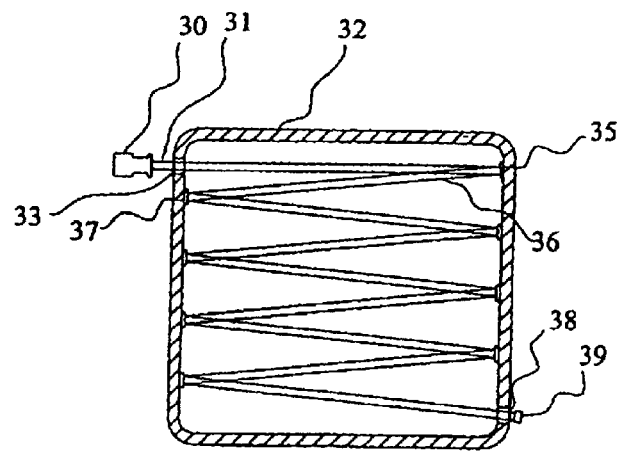
Figure 3
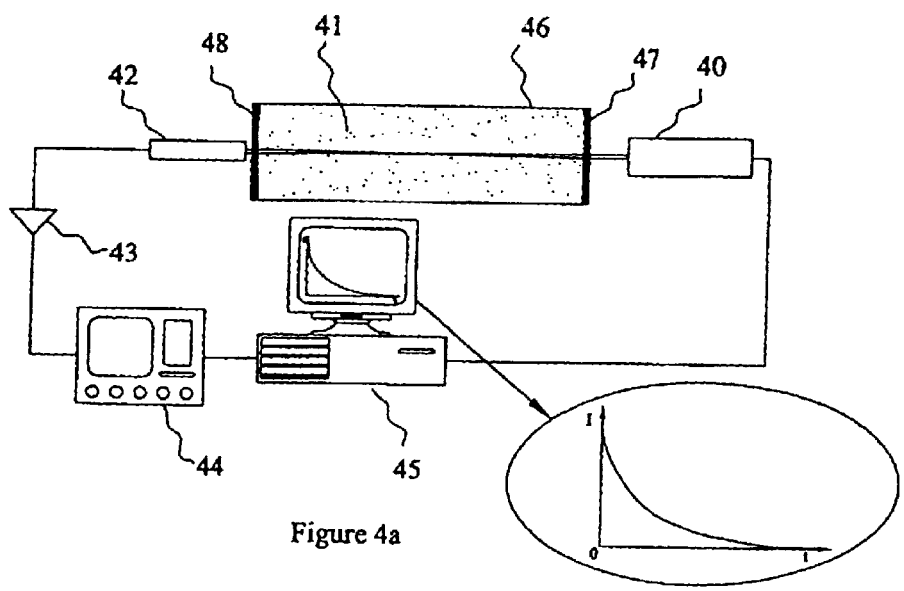
Figure 4a
Figure 4b

APPARATUS AND METHOD FOR MEASURING DECAY IN INTENSITY OF ELECTROMAGNETIC RADIATION IN MULTIPASS SPECTROMETRY

FIELD OF THE INVENTION

This invention relates to an apparatus and method for measuring decay in intensity of electromagnetic radiation passing through a radiation-absorbent sample due to absorption by the sample.

The apparatus and method can be used, inter alia, to obtain a value of a sample a parameter, such as the concentration of absorbent atoms or molecules related to the decay in intensity.

BACKGROUND OF THE INVENTION

Absorption Spectroscopy has long been a tool in the analytical chemists' repertoire of analytical techniques. The fundamental theory is based on the observation that atoms and molecules absorb energy from electromagnetic radiation of a particular wavelength, typically, but not exclusively in the form of photons passing through a sample. As each atom or molecule has a distinctive pattern of absorption wavelengths it is possible to deduce the atomic or molecular species under analysis. It is also possible to obtain a measure of the concentration of the species by means of reference to a calibration. The Beer-Lambert Law quantitatively relates the reduction in intensity of electromagnetic radiation of a particular wavelength to the concentration of absorbers (atoms or molecules) of that wavelength and the distance travelled by the electromagnetic radiation through the sample, by the expression:

$$I_d = I_o e^{-N\beta d} \qquad \text{Eq}^n 1$$

where N=the number of absorbers per unit volume.

β=the absorption coefficient.

$I_o$=the initial intensity of the source.

$I_d$=the measured intensity after passing through the sample.

d=the distance travelled through the sample.

This can be rearranged as follows:

$$N = \frac{1}{\beta d} \text{Ln}\left(\frac{I_o}{I_d}\right) \qquad \text{Eq}^n 2$$

Conventional Absorption Spectroscopy has a number of limitations. Although theoretically very sensitive and potentially quantitative, practical limitations imposed by current instrumentation and the method of measurement seriously restrict these capabilities and hence limit the application of absorption spectroscopy. One of these limitations is sensitivity of the measurement technique. From analysis of eqn. 1 it can be shown that there is an optimal range of values for the exponential term βNd. It is then clear that for a given value of β and in order to maintain the optimal value of the expression a reduction of the number of absorbers N must be compensated for by a corresponding increase in the value of d. Further analysis shows that for very small values of N, d can become impractically large. Long path lengths are achieved by means of folded geometries which are described in more detail later. It is also possible to deduce an effective dynamic range for a given instrumental configuration from eqn 1.

Further practical limitations in electromagnetic source stability over both short and medium term time scales and limitations in detection systems impose further limitations on sensitivity and accuracy of measurements. From Eqn 2 it can be demonstrated that there is a need for high accuracy of measurement in both $I_0$ and $I_d$. Since radiation sources have limited stability as stated previously, for the most accurate measurement both $I_0$ and $I_d$ must be measured simultaneously. This introduces additional cost and complexity to instrumentation. Both limitations described have partial solutions that are implemented in current instrumentation.

Further limitations become apparent in issues of quantification and reproducibility of measurements. These limitations arise from a combination of some of the previously described practical limitations and from the two point measurement system using $I_0$ at the source and $I_d$ at the end of the propagation path through the sample.

Many techniques have been devised with the objective of improving the performance of absorption spectroscopy. These include the use of folded path analysis cells that extend the optical path through the sample and thereby improve sensitivity, the use of detector arrays for spectroscopic analysis and the use Cavity Ringdown Laser Absorption Spectroscopy.

A paper by J. U. White in J. Opt. Soc Am, Vol 32, pp 285–288 describes a geometrical arrangement for extending the pathlength of a light source through an absorption cell by use of multiple reflections and traversals through the sample volume, thereby achieving an extended optical path in a small volume. This type of geometry has been widely adopted in absorption spectroscopy and is referred to as either a White cell or more generically as a folded path geometry cell. FIG. 1 of the accompanying drawings shows a typical folded path cell geometry. A light source 11 produces a light beam 12 which enters the cell 13 through a window 14 that is optically transparent at a wavelength of interest. The light beam 12 within the cell 13 is allowed to traverse the cell until it is incident upon mirror 15 where it is focused and redirected as a beam 16 towards a second optically transparent window 17 and thence to the detector 18. The main advantage of this geometrical arrangement is to increase the pathlength through the cell thereby increasing the sensitivity of the absorption measurement, as previously discussed. Many variations on this type of geometry have been devised including multiple reflection types. All have at least one common feature; that is, detection is carried out at the end of the propagation path of the light beam through the sample.

Another example of a multiple-pass cell is described in U.S. Pat. No. 5,220,402. As shown in FIG. 2 of the accompanying drawings, this arrangement comprises a focused light source 21 that is directed into a circular cell 22 through a wedge-shaped lens 23 that also acts as a window into the cell. The internal structure of the cell 22 is such that it provides some focusing of the light in both axial and radial planes giving a focal point close to the axis of the cell. By way of illustration, FIG. 2 shows one of a plurality of paths that the light might follow inside the cell. Light entering the cell through the lens 23 is directed to be incident on a reflecting surface 24 of the cell where it undergoes a reflection 25 directing it back through the axial region of the cell to a farther reflection point on the housing wall. This process continues until the light exits the cell through a further lens 26 where it is directed to a means of measurement 27. The primary aim is to maximise the optical path length within a cell of given volume, and both two and three dimensional geometries are described.

U.S. Pat. No. 5,485,276 describes another arrangement for increasing the optical path length of light within a gas absorption cell using multiple reflections and a collimated beam. As shown schematically in FIG. 3, this arrangement comprises a diode laser 30 producing a collimated beam 31 which enters a gas absorption cell 32 through an aperture or window 33. The collimated beam 31 inside the cell 32 is so directed that it is incident upon a mirror 35 on the opposite side of the cell 32. The mirror is angled so that the reflected beam 36 is then directed towards a further mirror 37 positioned on the same side as the entrance aperture, but displaced from it. During traversal between mirrors, the light suffers a loss in intensity due to absorption by absorbing fluid in the cell. Further reflections and traversals continue in a like manner until the light exits the cell at an exit aperture 38 whereupon it is detected by a detector 39. The mirrors are all contained within a two dimensional plane.

In general, these folded path geometries have been used for the purpose of increasing the path length of the light through a sample in order to improve measurement capability for low concentrations in absorbance spectroscopy.

It is also known to use multiple detectors in spectroscopy, primarily in detector arrays used for measuring spectra. For example, U.S. Pat. No. 5,721,430 describes an apparatus that uses multiple detectors in an NDIR analayser and a wideband light source. These multiple detectors are configured to operate in parallel at the end of the optical pathlength, and the detectors are provided with individual optical bandpass filters enabling them to detect different wavelengths.

Another arrangement using multiple detectors at the end of the propagation path through the sample is described in U.S. Pat. No. 5,854,684. In general, multiple detectors have been used for the purpose of measuring different wavelengths in a spectroscopic instrument after either an optical filter system or the application of a wavelength dispersive device.

A recent development in the field of high sensitivity optical spectroscopy is Cavity Ringdown. The technique of Cavity Ringdown is derived from the high finesse optically resonant cavities used in laser technology and uses the principle of a highly resonant optical cavity in the measurement of low concentrations of gases. In Cavity Ringdown the laser light is introduced into the cavity from an external laser source. Cavity Ringdown has its roots in a paper by J. M. Herbelin et al published in the J. Appl. Opt. 19(1) p 144–147 in 1980 in which he describes the measurement of the reflectivity coefficient of high performance mirrors using a cavity attenuated phase shift (CAPS) technique. The mirrors being measured form the ends of the optically resonant cavity. In the described CAPS technique the cavity decay time (deduced from the induced phase shift) is used to calculate the reflectivity coefficients of the mirrors. In the paper, concerns were raised about the potential distortion of the calculations of the coefficients by small quantities of absorbing contaminant gases in the optically resonant cavity. It was further noted that the CAPS technique may have application in the measurement of the concentrations of small quantities of gas deliberately introduced into the optically resonant cavity. A paper by D. Z. Anderson et al published in Appl. Opt. 23(8) p 1238 in 1984 describes a further development in which the decay of light intensity with time is directly observed.

The advent of high performance, fast pulsed lasers obviates the need for attenuated phase shift measurements, and a paper by A. O'Keefe et al in Rev Sci Inst, 1988, 59(12), p2544 describes the use of pulsed lasers and the measurement of decay in intensity with time of the pulse intracavity. All subsequent developments in cavity ringdown techniques are based on variations of this basic approach. A review of the work of Herbelin et al and of the subsequent developments is contained in a paper by J. J. Scherer et al in Chem Rev 1997, v 97, pp25–51.

A typical cavity ringdown apparatus, is now described by reference to FIGS. 4a and 4b. The apparatus consists of laser 40, a high finesse resonant optical cavity 41, a photon mulitplier 42, an amplifier 43, an oscilloscope 44 and a computer 45. The optical cavity consists of an outer housing 46, typically a cylinder, and two high reflectivity concave mirrors 47,48 that are additionally used to seal the ends of the cavity 41. The mirror 47 nearest the laser 40 is called the entrance mirror and the mirror 48 at the other end the exit mirror. The mirrors 47,48 have a coefficient of reflectivity, R, which is typically of the order of 0.995 or higher. The cavity contains an absorbant gas species for analysis by absorption of photons.

The oscilloscope 44 is used to digitise the amplified signal from the photon multiplier 42 and the computer 45 is used for general control of the timing electronics and for recording the digitised output from the oscilloscope.

In a typical cavity ringdown experiment, a fast (of the order of nanoseconds) pulse of laser energy of a known wavelength is focused and directed into the optical cavity through the entrance mirror 47. A small amount of the laser energy equal to (1-R), is coupled into the cavity and the rest of the laser energy is reflected back from the mirror and has no further function in the measurement. The light in the cavity is now trapped and reflects back and forth between the two mirrors 47,48. A small fraction (1-R) of the trapped laser energy passes through each mirror at each reflection. By measuring the small component (1-R) of the light that is transmitted through the exit mirror 48 after each traversal through the cavity as a function of time t, a measure of the decay of the light pulse can be made. This decay with time I(t) is due a combination of reflection losses and absorption by the gas contained in the cavity. This measured intensity can be shown to be proportional to the losses in the cavity where, $$I(t) \propto R_{tot} e^{-\sigma(\lambda)Nt} \qquad \text{Eqn3}$$

Equation 3 has the form of the Beer-Lambert law which relates the losses due to absorption to the number of absorbers present in the cavity, but is modified to allow for the additional losses due to multiple reflections, where $R_{tot}$ is the total loss coefficient due to the reflections. A typical decay curve is shown in FIG. 4b. By calibrating the apparatus with no absorbing gas present, a value for $R_{tot}$ due solely to reflection at the mirrors can be determined. This value can then be taken into account in the measurement of the decay when an absorbing gas is present, and the number of absorbers determined. Decay times for a typical cavity ringdown measurement are usually in the region of the one to tens of microseconds, in part dependent upon the cavity length and also on the concentration of absorbers present.

A drawback of the cavity ringdown technique is the requirement to measure the decaying intensity of electromagnetic radiation as a function of time, typically over a time interval which is only of the order of tens of microseconds. Accordingly, implementation of cavity ringdown techniques is both complex and expensive, requiring the use of fast pulsed lasers, high finesse, high Q optical cavities and high speed digital timing electronics.

The cavity ringdown technique also has the disadvantage that the pulsed electromagnetic radiation undergoes multiples passes through the same sample region, and this may reduce the sensitivity of the measurement being made.

Another major problem associated with the use of cavity ringdown is the poor efficiency of coupling of the electromagnetic radiation into the optical cavity. U.S. Pat. No. 5,815,277 describes a method for alleviating this problem. In this method, an acoustic optical modulator (AOM) is placed inside the cavity in order to redirect the light pulse onto the optical axis of the resonant cavity. This increases the coupling efficiency to in excess of 40%. Although this approach gives significant improvements in efficiency, it does introduce an additional optical component into the cavity which may decrease the effectiveness of both the measurement and its applicability. The AOM adds to the cost and to the complexity of the control system, factors which must be considered against a reduction in the requirements for the initial energy of the laser source and the potential to use lower cost detection methods.

A further recent development in the use of cavity ringdown is a technique known as Intracavity Laser Spectroscopy (ILS) where the laser cavity itself is used as the analysis cell. This type of device has many advantages in terms of size and sensitivity, but is still limited in its applicability. U.S. Pat. Nos. 5,841,533, 5,742,054 and 5,747,807 describe three examples of the application of this technique.

It is an object of the present invention to provide an apparatus and method for measuring decay in intensity of electromagnetic radiation passing through a radiation-absorbent sample due to absorption by the sample which at least alleviates the above-described short-comings of existing arrangements.

SUMMARY OF THE INVENTION

According to one aspect of the present invention there is provided an apparatus for measuring decay in intensity of electromagnetic radiation passing through a radiation-absorbent sample due to absorption of radiation by the sample, comprising a source of electromagnetic radiation having a wavelength within an absorption band of the sample, partially-reflective means for partially reflecting said electromagnetic radiation at successive positions which are spaced apart from each other along a predetermined path through the sample, said partially-reflective means being effective at each said successive position to separate incident radiation into a reflected part which is caused by the partially-reflective means to follow said predetermined path and an unreflected part, and derivation means for deriving a value of said decay from measurements of intensity of the unreflected parts of the electromagnetic radiation produced at a number of different said positions along said predetermined path.

According to another aspect of the invention there is provided a method for measuring decay in intensity of electromagnetic radiation passing through a radiation-absorbent sample due to absorption of radiation by the sample, comprising, generating electromagnetic radiation having a wavelength within an absorption band of the sample, partially-reflecting said electromagnetic radiation at successive positions which are spaced apart from each other along a predetermined path through the sample, whereby to separate the radiation into a reflected part which is caused to follow said predetermined path and an unreflected part, and deriving a value of said decay from measurements of intensity of the unreflected parts of the electromagnetic radiation produced at a number of different said positions along said predetermined path.

BRIEF DESCRIPTION OF THE DRAWINGS

Embodiments of the invention are now described, by way of example only, with reference to the accompanying drawings of which:

FIG. 3 is a schematic representation of another known gas absorption cell, FIG. 4a is a schematic representation of a known cavity ringdown apparatus, FIG. 4b shows a typical decay curve obtained using the apparatus of FIG. 4a, FIG. 5 is a schematic representation of a measuring apparatus according to the invention.

DETAILED DESCRIPTION OF THE PREFERRED EMBODIMENTS

Figure 1:
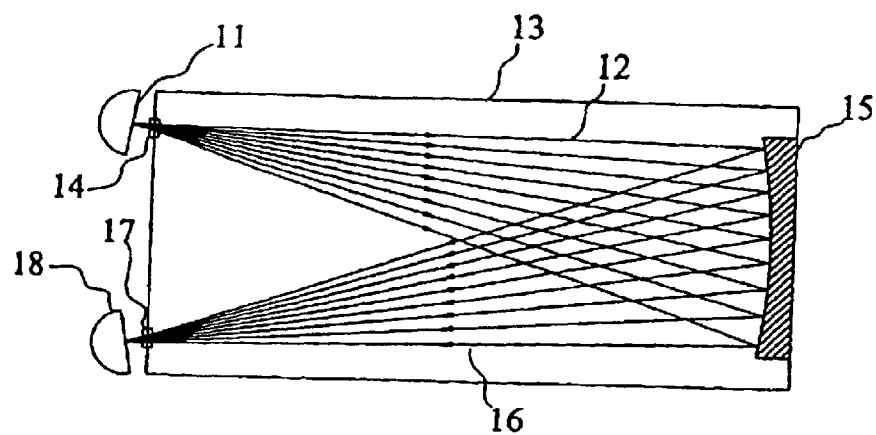
FIG. 1 is a schematic representation of a known, folded-path geometry absorption cell.
Figure 2:
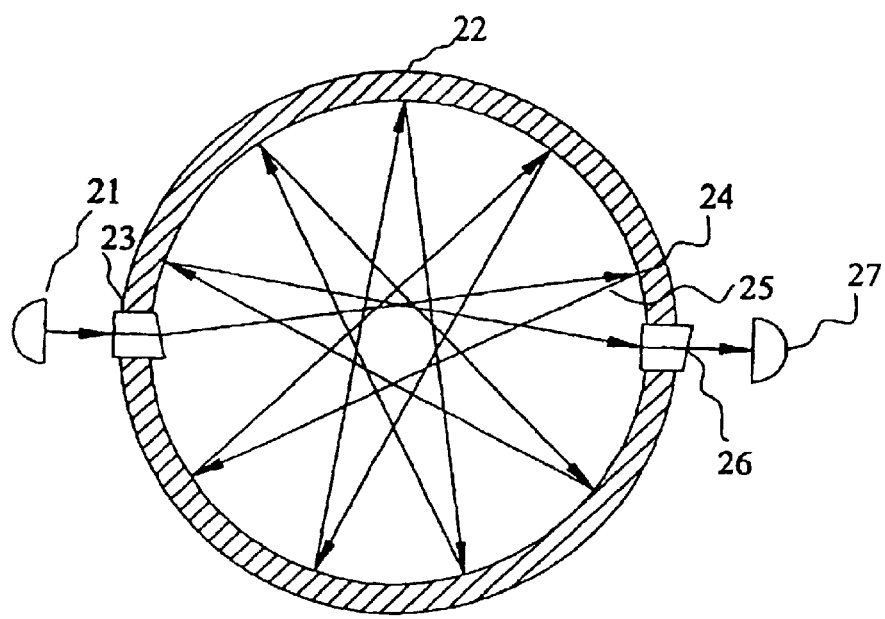
FIG. 2 is a schematic representation of a known multiple-pass absorption cell.
Figure 5:
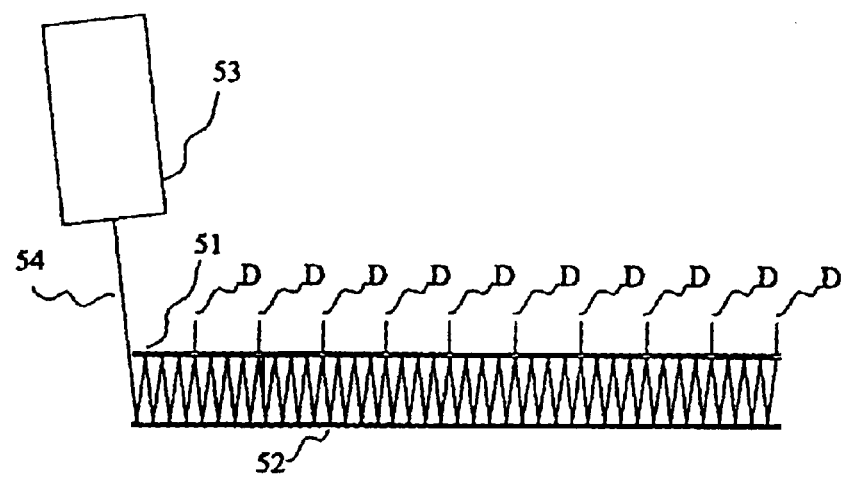

FIG. 5 shows a schematic representation of an embodiment of the invention.

The apparatus shown in FIG. 5 comprises two parallel, flat, partially-reflective mirrors 51,52 having a configuration akin to a Fabry Perot resonator. A source 53 directs a beam 54 of electromagnetic radiation onto the facing surface of mirror 52. The beam is incident on this surface at a small angle (typically less than 10°) with respect to the normal and so undergoes multiple reflections between the facing surfaces of the mirrors, as shown in the drawing.

With this arrangement, the beam 54 is constrained to follow a predetermined, extended path between the mirrors, being alternately reflected at each mirror at successive positions spaced apart equidistantly from each other along the path.

A number of detectors is provided to measure the unreflected parts of the electromagnetic radiation at different positions D along the extended path followed by the beam. As will be described in greater detail hereinafter with reference to FIG. 6, these measurements can be used to derive a value of decay of intensity of electromagnetic radiation due to absorption by a radiation-absorbent sample contained between the mirrors 51,52. As will be explained, because the path length d between successive positions D can be accurately measured, a value of decay due to absorption can be derived without any need to measure intensity as a function of time t, although the timing of each measurement can still be calculated by application of the simple relationship t=d/nc, where n is the refractive index of the sample and c is the speed of light in vacuum.

Therefore, in comparison with known cavity ringdown arrangements described hereinbefore, which do rely upon time-based measurements, the apparatus of FIG. 5 offers reduced complexity and cost, and does not require fast timing electronics which may be susceptible to timing jitter. In contrast, the apparatus of FIG. 5 relies on the accurate measurement of path length of between successive detection positions D.

Figure 6:
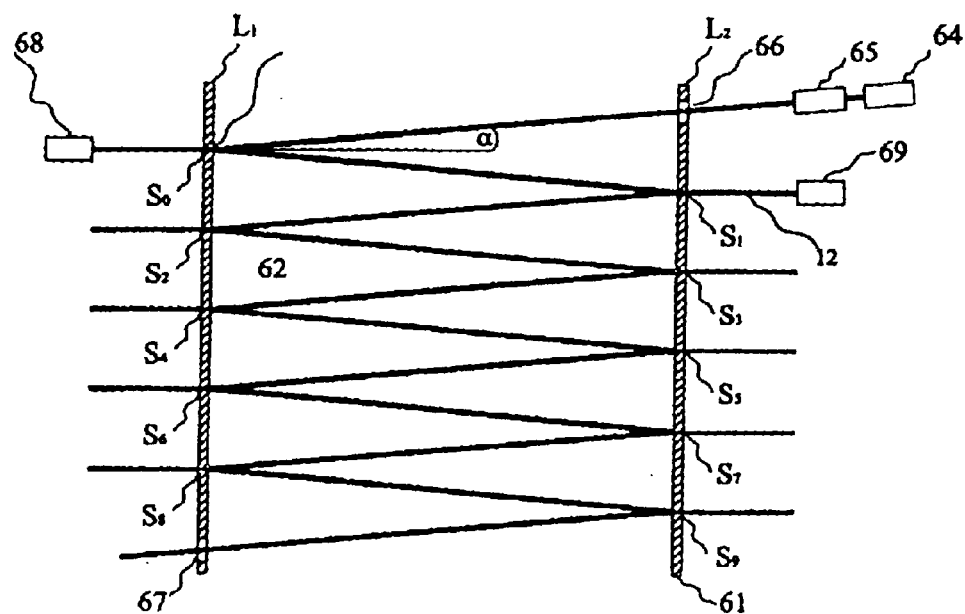
FIG. 6 shows another embodiment of a measuring apparatus according to the invention.

FIG. 6 shows another embodiment of the invention. Referring to this Figure, the measuring apparatus includes a chamber 61 enclosing a sample region 62, and a plurality of inwardly-facing, partially-reflective specular surfaces $S_0$, $S_1 \ldots S_9$ supported by, or forming part of, the chamber wall. For clarity of illustration, only ten such surfaces are shown. The chamber 61 may include an inlet unit (not shown) for controllably admitting sample to the sample region 62 and an outlet unit (not shown) for controllably discharging sample from the sample region.

The apparatus also includes a source 64 of pulsed electromagnetic radiation and an optical element 65 for focusing and calibrating the pulses causing them to enter the chamber 61 at a desired angle of incidence α via a radiation transparent window 66.

In this particular embodiment, the source 64 is a laser producing a monochromatic beam of light. However, it will be appreciated that any other suitable source of electromagnetic radiation may be used, and such sources may include single monochromatic, multiple monochromatic or wide band sources that are either static or wavelength scanned. It is also envisaged that the source may be able to produce wavelengths in the range of 2 nm to 10 mm, dependent on the absorption bands of the sample.

Furthermore, in this particular embodiment the means of measurement of the decay in intensity of the electromagnetic radiation is by photon detectors used in a single wavelength detection mode. However it will again be appreciated that any suitable detectors for the wavelength(s) used may be usefully employed and additionally said detectors may be combined with some wavelength dispersive or discrimination device to provide a spectroscopic output.

Additionally, this method of measurement may also be applied to other spectroscopic techniques which require the manipulation of the input electromagnetic radiation such as Fourier transform or other like techniques.

The specular surfaces $S_0, S_1 \ldots S_9$ are divided into two groups $S_0, S_2 \ldots S_8; S_1, S_3 \ldots S_9$ arranged along two parallel lines $L_1, L_2$.

The relative spacings and orientations of the specular surfaces and the angle of incidence α of the pulses entering the chamber 61 via window 66 are so chosen that the pulses undergo multiple reflections, causing them to follow a predetermined path through the sample region 62. Thus, as shown in FIG. 6, a pulse incident at specular surface $S_0$ is reflected back through the sample region 62 to impinge on specular surface $S_1$ which, in turn, reflects the incident pulse back through the sample region to impinge in specular surface $S_2$, and so on, until, eventually, the pulse exits the chamber 61 via an exit window 67 or its intensity falls to zero.

In this manner, an incident pulse of electromagnetic radiation follows a predetermined path having an extended, folded configuration, passing back and forth through different parts of the sample region, giving improved sensitivity.

Figure 7:
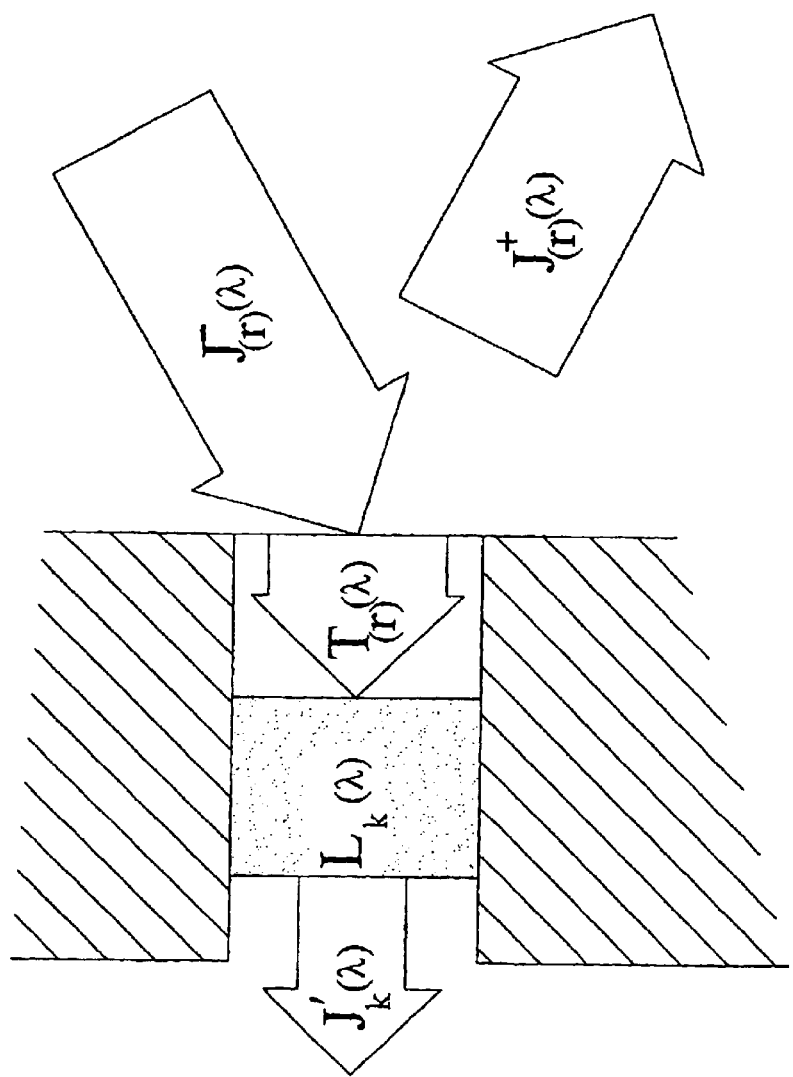
FIG. 7 is a schematic representation of a specular surface in the measuring apparatus of FIG. 6.

Referring now to FIG. 7, each specular surface $S_r$ is effective to separate the incident photon flux $J_r^-(\lambda)$ into a reflected part $J_r^+(\lambda)$ and a non-reflected part $T_r(\lambda)$, where $\lambda$ is the wavelength of the incident photons.

As will now be explained, the intensity of an incoming pulse (i.e. the photon flux) progressively decays as it passes through the sample region 62. This decay is attributable to two different effects; firstly, as already described, each specular surface separates an incident pulse into a reflected part and a non-reflected part and so the intensity of radiation in the pulse will be reduced at each reflection; and secondly, radiation in the reflected part of the pulse will be progressively absorbed by the radiation-absorbent sample through which it passes.

The relative spacings d of the specular surfaces along the predetermined path are precisely known and this can be exploited to derive a value of decay of intensity attributable to the second, sample-absorbent effect. This is accomplished by measuring the non-reflected parts of the radiation produced at some or all of the specular surfaces. To this end, a suitable detector is provided behind each specular surface where a measurement is to be made. For clarity of illustration, only two such detectors 68,69 are shown in FIG. 6, located behind specular surfaces $S_0$, $S_1$ respectively.

It will be clear from FIG. 7, that the non-reflected part of the incident photon flux $T_r(\lambda)$ (at the $r^{th}$ specular reflector) is given by the expression:

$$T_r(\lambda)=J_r^-(\lambda)(1-R(\lambda)) \qquad \text{Eq4}$$

where R(λ) is the wavelength-dependent reflection coefficient of the reflective surface;
and that the reflected part $J_r^+(\lambda)$ is given by the expression:

$$J_r^-(\lambda)=J_r^-(\lambda)R(\lambda) \qquad \text{Eq5}$$

Between the $r^{th}$ and the $(r+1)^{th}$ specular surfaces the reflected part of the photon flux will undergo a reduction due to absorption by the sample, and it can be shown that this reduction is governed by the Beer-Lambert relationship, given by the general expression:

$$J_{r+1}(\lambda)=J_r(\lambda)e^{-\sigma(\lambda)Nd} \qquad \text{Eq6}$$

where N is the total number of absorbers per unit volume at a given wavelength λ, d is the path length between specular surfaces and σ (λ) is the wavelength dependent absorption cross-section.

In the following analysis, an index k (=0, 1, 2 . . . ) is used to denote each successive detector which is provided behind a specular surface to measure the photon flux of the unreflected part of the electromagnetic radiation. Detectors may be provided behind all the specular surfaces, and the index k of each detector would then be the same as the index r of the associated surface. However, detectors may be provided behind some, but not all of the reflectors and, in this case, the index k of a detector may not be the same as the index r of the associated surface, subject to the initial condition that r=k=o.

It is possible to show that the reflected photon flux $J_r^+(\lambda)$ at the $r^{th}$ specular surface is given by the expression:

$$J_r^+(\lambda)=J_0(\lambda)R(\lambda)^r e^{-\sigma(\lambda)rNd}, \qquad \text{Eq7}$$

where $J_0$ (λ) is the photon flux incident at the first specular surface (r=0).

It can also be shown that the unreflected part of the photon flux $J_k(\lambda)$ measured by the $k^{th}$ detector located behind the $r^{th}$ specular surface is also governed by the Beer-Lambert relationship, given by the general expression:

$$J_k'(\lambda)=J_0'(\lambda)R(\lambda)^r e^{-\sigma(\lambda)rNd}, \qquad \text{Eq8}$$

where $J_0'(\lambda)$ is related to $J_0(\lambda)$ by the expression:

$$J_0(\lambda) = \frac{J_0'(\lambda)R(\lambda)}{L_0(\lambda)(1-R(\lambda))} \qquad \text{Eq9}$$

where $L_0(\lambda)$ is the loss of photon flux due to transmission at the first specular surface (r=0). Formal derivations of the expressions given by Equs 7, 8 and 9 are given hereinafter.

It will be apparent from equ 7 above that the function Ln $(J_k'(\lambda))$ is linearly related to rd and because, in this embodiment, a detector is provided at each specular surface (i.e. k=r) the function Ln $(J_k'(\lambda))$ is linearly related to k also.

Figure 8A:
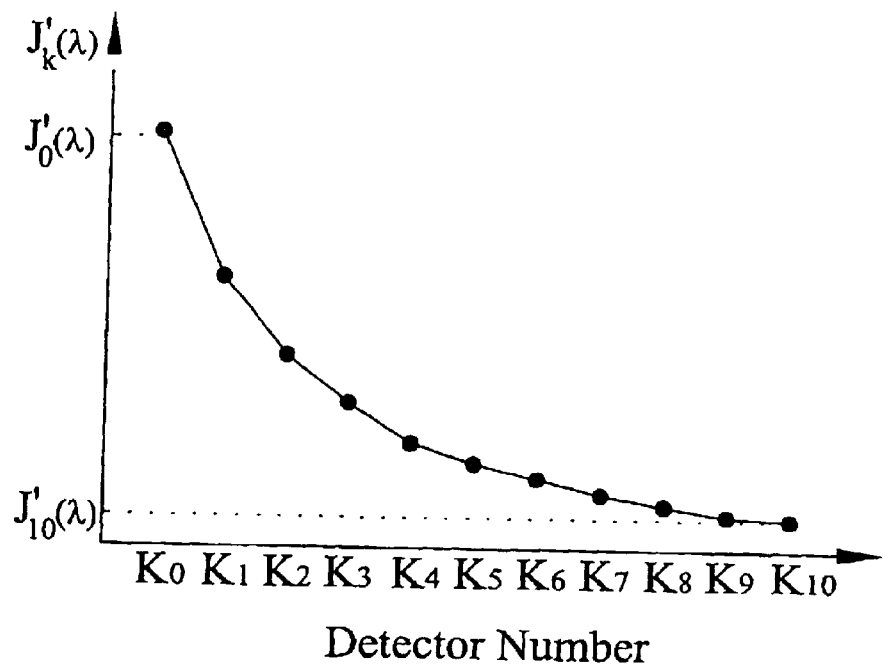
FIG. 8a shows a decay curve obtained using the apparatus of FIG. 6.
Figure 8B:
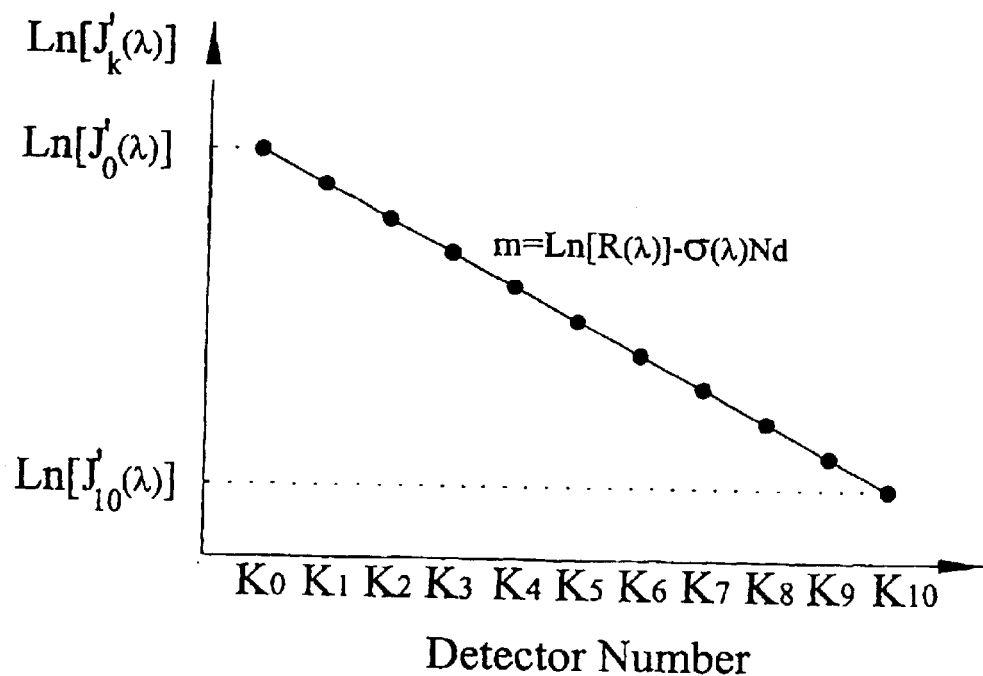
FIG. 8b shows a further curve obtained from the decay curve of FIG. 8a, and FIGS. 9, 10 and 11 are diagrams useful in understanding the derivation of certain mathematical expressions referred to in the description.

FIG. 8a shows the decay curve formed by a plot of $J_k'(\lambda)$ as a function of detector number k, and FIG. 8b shows the corresponding plot of Ln $(J_k'(\lambda))$ as a function of k. The slope m of the plot shown in FIG. 8b is given by the expression:

$$m = Ln(R(\lambda)) - \sigma(\lambda)Nd, \qquad \text{Eq 10}$$

from which the decay value $\sigma(\lambda)Nd$ due to absorption can be readily determined.

Furthermore, provided the value of $\sigma(\lambda)$ is known, the concentration of absorbers N can also be determined.

It will also be noted that the value of m is independent of the initial photon flux $J_0(\lambda)$. Therefore, a decay value can be derived without reference to the initial intensity of the electromagnetic radiation. Accordingly, the described apparatus does not suffer from the problems caused by fluctuating source sensitivity encountered in some of the earlier systems described hereinbefore. Some of the limitations regarding quantification and comparability are also alleviated.

As already explained the described embodiments of this invention do not rely on the relative timings of the measurements. Therefore, in comparison with the known cavity ringdown techniques which do rely on time-based measurements, the described embodiments offer reduced complexity and cost, and do not need fast timing electronics which may be susceptible to timing jitter. The described embodiments also have the further advantage that they do not require a high finesse resonant cavity with its attendant coupling problems; in contrast, electromagnetic radiation can be introduced into the sample region with relative ease and high efficiencies approaching 100% using an appropriately angled beam. Furthermore, the electromagnetic radiation does not pass repeatedly through the same sample region; in contrast, the electromagnetic radiation follows a path extending through different parts of the sample region, giving improved sensitivity.

The described embodiments have a folded-path geometry thereby increasing the path length within a relatively compact sample region. An increased path length also gives improved sensitivity and this is particularly advantageous in the case of a sample having a low concentration of absorbers. However, the described embodiments do not rely upon a single detector located at the end of the optical path which is used in known folded-path arrangements and which tends to limit the accuracy and precision of the measurements. In contrast, the decay value is derived from intensity measurements made at a number of different positions along the optical path, giving improved precision and an extended dynamic range.

Although the described example demonstrates how the invention may be used to determine the concentration N of absorbers in the sample, the invention may also be used to determine other sample parameters; for example, sample parameters associated with variations of bonding, excitation or rotational state giving rise to an identifiable absorption band.

Furthermore, although the described embodiments have a two-dimensional, folded path geometry, three-dimensional, folded path geometries are also envisaged.

In the described embodiments, the specular surfaces are spaced apart from each other equidistantly, with a separation d. However, the reflectors (and their associated detectors) need not necessarily be spaced apart equidistantly. In the case of non-equidistantly-spaced reflectors the term rd in Equ 8 would be replaced by the term $d_r$ representing the actual distance of $r^{th}$ reflector along the optical path, and the function Ln $(J_k'(\lambda))$ would then be linearly related to $d_r$.

There now follows derivations of Equations 7, 8, 9 and 10 above.

Derivation of Equation 7

Figure 9:
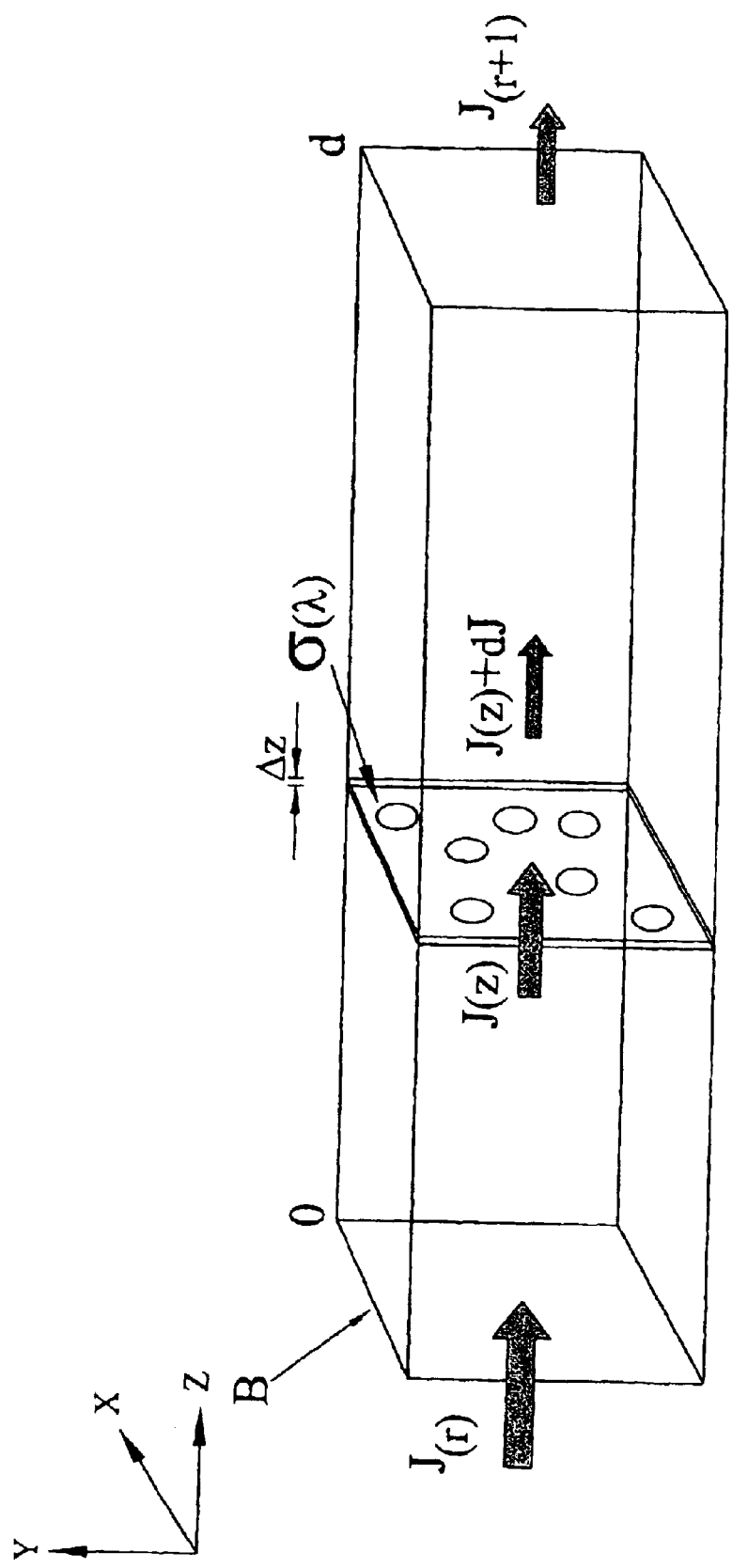

Referring to FIG. 9, the photon flux is incident upon the area B and passes through the volume which contains the absorbing gas species.

We define the following parameters.

$J_{(r)}(\lambda)$ is the photon flux entering the volume. (r=0, 1, 2 ...)

$J_{(r+1)}(\lambda)$ is the photon flux leaving the volume at z=d $J(z,\lambda)$ is the photon flux at any point z along the z axis between 0 and d N is the number of absorbers per unit volume.

B is the cross sectional area of the volume.

$\sigma(\lambda)$ is the effective, wavelength dependent, absorption cross sectional area.

d is the path length between reflections

The number of absorbers per unit length is given by NB

We can derive the value for $\Delta J$ as:

$$-dJ(\lambda) = \frac{J(z,\lambda)[\sigma(\lambda)NBdz]}{B}$$

Therefore the ratio of absorption is given by:

$$\frac{dJ(\lambda)}{J(z,\lambda)} = -\sigma(\lambda)Ndz$$

Integrating this over the range of z for the volume gives $$\int_{J_{(r)}(\lambda)}^{J_{(r+1)}(\lambda)} \frac{1}{J(z)} dJ(\lambda) = -\sigma(\lambda)N \int_0^d dz$$

$$Ln(J_{(r+1)}(\lambda)) - Ln(J_{(r)}(\lambda)) = -\sigma(\lambda)Nd$$

Taking the exponential of both sides gives:

$$\frac{J_{(r+1)}(\lambda)}{J_{(r)}(\lambda)} = e^{-\sigma(\lambda)Nd} \qquad \text{Eq}^n 11$$

So the photon flux at z=d is given by $$J_{(r+1)}(\lambda) = J_{(r)}(\lambda)e^{-\sigma(\lambda)Nd} \qquad \text{Eq}^n 12$$

Figure 10:
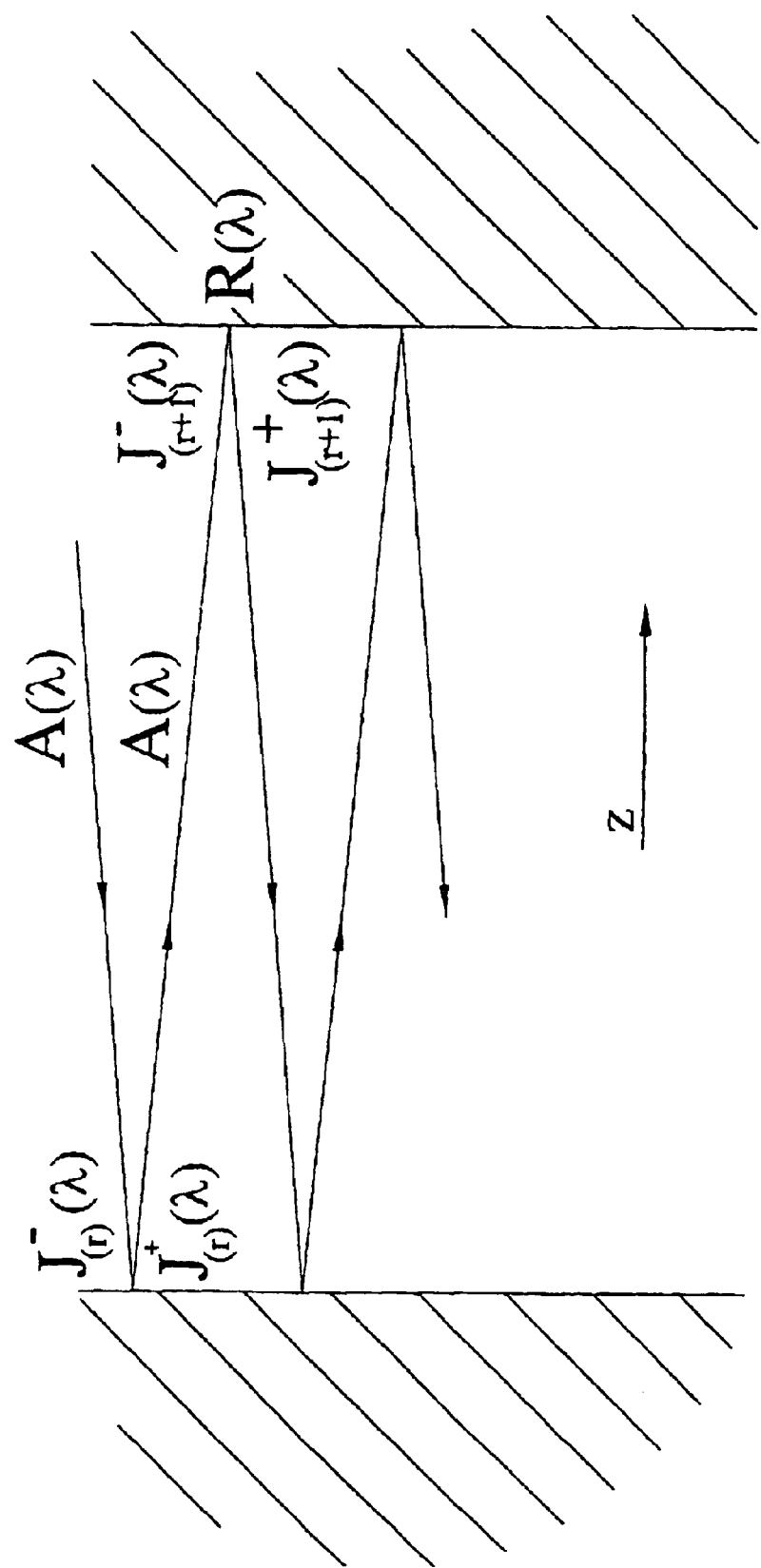

Referring to FIG. 10. we can now consider the case of a reflection at z=d where $J_{(r+1)}^-(\lambda)$=The photon intensity at reflection r+1 just before the reflection occurs.

$J_{(r+1)}^+(\lambda)$=The photon intensity at reflection r+1 just after the reflection occurs.

(in between $J_{(r+1)}^-(\lambda)$ & $J_{(r+1)}^+(\lambda)$ the losses in photon flux due to absorption by gas is assumed to be zero).

$R(\lambda)$=the wavelength dependent reflectivity coefficient.

$A(\lambda)$=is the wave length dependent absorption of the sample gas r is the number of reflection events.

From FIG. 10 we see that $$J_{(r+1)}^+(\lambda) = R(\lambda)J_{(r+1)}^-$$

$$= R(\lambda)J_{(r)}^+(\lambda)A(\lambda) \qquad \text{Eq}^n 13$$

$$= R(\lambda)J_{(r)}^+(\lambda)e^{-\sigma(\lambda)Nd} \qquad \text{Eq}^n 14$$

Equation 14 is the general expression for the decay in photon flux caused by a single absorption followed by a single reflection at a mirror surface.

W can now expand this for multiple reflections and we see that, for r successive absorptions and reflections from $J_{(0)}^{+}(\lambda)$ to $J_{r+1}^{+}(\lambda)$ we have:

$$J_r^{+}(\lambda) = J_{(0)}^{+}(\lambda)[R(\lambda)A(\lambda)]^r$$

We can now define $J_0(\lambda)$ as being the photon flux immediately after the zeroth reflection where r=0 such that $$J_0(\lambda) = J_0^{+}(\lambda)$$

The general expression for r absorptions and reflections can be written as $$J_r^{+}(\lambda) = J_0(\lambda)[R(\lambda)A(\lambda)]^r \qquad \text{Eq}^n 15$$
$$= J_0(\lambda)R(\lambda)^r e^{-\sigma(\lambda)rNd}$$

$$J_r^{-}(\lambda) = J_0(\lambda)R(\lambda)^{r-1}A(\lambda)^r \qquad \text{Eq}^n 16$$
$$= J_0(\lambda)R(\lambda)^{(r-1)} e^{-\sigma(\lambda)rNd}$$

Derivation of equations 8, 9, & 10

In order to demonstrate the decay function, we need to define the relationship between the measured photon flux at detector k related to the initial photon flux $J_0(\lambda)$. Since each detector is uniquely associated with a reflection r (r not necessarily being equal to k) then we can define the following parameters and initial conditions.

Let each detected photon flux be $J_k^{+}(\lambda)$

Let each detector be k where k=0, 1, 2 ... K and the initial condition of r=k=0

So $$J_k^{+}(\lambda) = T_r(\lambda)L_k J_r^{-}(\lambda) \qquad \text{Eq}^n 17$$

where:

$L_k(\lambda)$=the total transmission loss between the unreflected component and the detector k.

Figure 11:
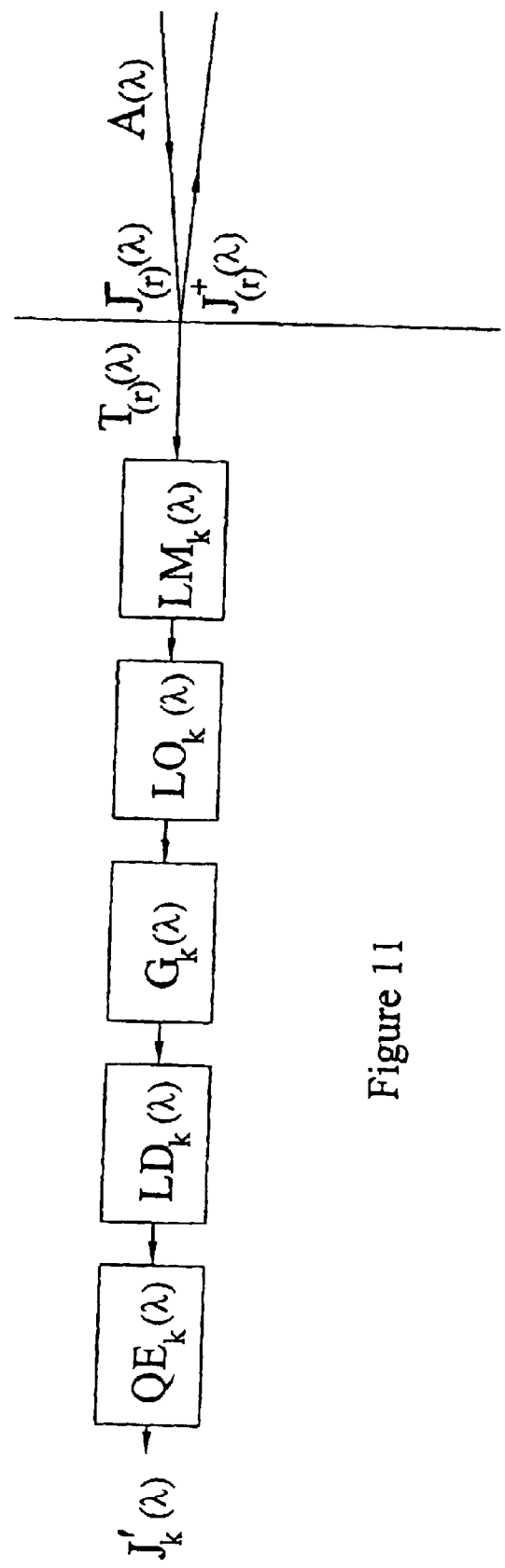

And $T_r(\lambda)$=the total of the unreflected component of the incident photon flux at reflection r Now from FIG. 11

$$T_r(\lambda) = J_r^{-}(\lambda) - J_r^{+}(\lambda)$$
$$= J_r^{-}(\lambda) - J_r^{-}(\lambda)R(\lambda)$$
$$= J_r^{-}(1 - R(\lambda))$$

substituting for $J_r^{-}(\lambda)$ from Eq$^n$ 16 gives:

$$T_r(\lambda) = J_0(\lambda)R(\lambda)^{(r-1)}e^{-\sigma(\lambda)rNd}(1-R(\lambda)) \qquad \text{Eq}^n 18$$

We can now include transmission coefficients related to the $k^{th}$ detector position.

From FIG. 11

$$L_k(\lambda) = LO_k(\lambda)LM_k(\lambda)LD_k(\lambda)QE_k(\lambda)G_k(\lambda) \qquad \text{Eq}^n 19$$

where:

$LM_k(\lambda)$=is the wavelength dependent transmission coefficient through the mirror.

$LO_k(\lambda)$=is the collective wavelength dependent optical transmission coefficients related to any optical elements between the mirror and any dispersive device or detector $G_k(\lambda)$=is the wavelength dependent dispersion characteristics of any dispersive device. In the absence of a dispersive device, $G_k(\lambda)=1$ $LD_k(\lambda)$=is the wavelength dependent detector transmission coefficients $QE_k(\lambda)$=is the wavelength dependent quantum efficiency coefficient of the detector Substituting into Eq$^n$ 17 from 18 & 19 we obtain the expression.

$$J_k^{+}(\lambda) = LM_k(\lambda)LO_k(\lambda)LD_k(\lambda)QE_k(\lambda)G_k(\lambda)(1-R(\lambda)J_0(\lambda)$$
$$R(\lambda)^{r-1}e^{-\sigma(\lambda)rNd}) \qquad \text{Eq}^n 20$$

which can be simplified to the form:

$$J_k^{+}(\lambda) = J_0(\lambda)L_k(\lambda)(1-R)(\lambda)R(\lambda)^{r-1}e^{-\sigma(\lambda)rNd} \qquad \text{Eq}^n 21$$

It is useful for to rearrange this to obtain the value for the parameter N. The most convenient form is to plot a graph of $Ln(J_k^{+}(\lambda))$ against r.

Rearranging and taking logs of both sides we obtain the expression:

$$Ln\left(J_k'(\lambda)\right) = (Ln(R(\lambda)) - \sigma(\lambda)Nd)r + Ln\left(\frac{(1-R)(\lambda)L_k(\lambda)J_0(\lambda)}{(R(\lambda))}\right) \qquad \text{Eq}^n 22$$

Which is an equation of the form y=mx+c
Where $y = Ln(J_k^{+}(\lambda))$, $x = r$, $$c = Ln\left(\frac{J_0(\lambda)L_k(\lambda)(1-R(\lambda))}{R(\lambda)}\right) \text{ and}$$

$m = Ln(R(\lambda) - \sigma(\lambda)Nd)$

So we can derive the value of N, the absorption parameter from $$N = \frac{m - Ln(R)}{-\sigma(\lambda)d} \qquad \text{Eq}^n 23$$

We know the values R and d for a particular physical configuration and we can calculate (or have previously experimentally determined) the value of $\sigma(\lambda)$ m is found from the slope of the plot of $Ln(J_k^{+}(\lambda))$ with r.

For the case where there is a linear relationship between r and k then we can define the following instrument parameter C $$\text{Let } C = \frac{M}{K}$$

where M is the total number of reflections r
and K is the total number of detectors.
So r can be expressed in terms of C and k $r = Ck$ Substituting this into equation 22 changes the variable from r to k so that equation 23 is modified to be $$N = \frac{\frac{m}{C} - Ln(R(\lambda))}{-\sigma(\lambda)d} \qquad \text{Eq}^n 24$$

In a simple practical instrument this is the most convenient form to use where $Ln(J_k^{+}(\lambda))$ is plotted against the detector number k. We also see from the equation 24 that the measurement of the number of absorbers N is now shown to be independent of the initial light source intensity.

Referring back to FIG. 11 and equation 21 and setting r=k=0 we obtain an expression for $J_0^{+}(\lambda)$ where $$J_0(\lambda) = \frac{J_0(\lambda)R(\lambda)}{L_0(\lambda)(1-R(\lambda))} = \qquad \text{Eq}^n 25$$

We can now normalise to the photon flux $J_0^+(\lambda)$ measured at the first detector with that measured at the $k^{th}$ detector by dividing equation 11 by equation 19 as follows.

$$\frac{J'_k(\lambda)}{J'_0(\lambda)} = \frac{L_k(\lambda)(1-R(\lambda))J_0(\lambda)R(\lambda)^{r-1}e^{-\sigma(\lambda)rNd}R(\lambda)}{L_0(\lambda)(1-R(\lambda))J_0(\lambda)}$$

If the value of $L_k=L_0$ then the expression simplifies to:

$$J_k^+(\lambda)=J_0^+(\lambda)R(\lambda)^r e^{-\sigma(\lambda)rNd} \qquad \text{Eq}^n 26$$

For other applications, the photon flux can be replaced with an energy flux. This is more appropriate for the case of long wavelength radiation.

It is also noted that this proof is generally applicable to any fluid that substantially obeys the Beer-Lambert law.

This proof also can be extended to multiple absorptions where the term $A(\lambda)$ can be expanded to include contributions from more than one absorber at that wavelength. e.g. for a given wavelength $\lambda_1$ $$A(\lambda_l) = \sum_1^n a_n(\lambda_l) \qquad \text{Eq}^n 27$$

What is claimed is:

1. An apparatus for measuring decay in intensity of electromagnetic radiation passing through a radiation-absorbent sample due to absorption of radiation by the sample, comprising a source of electromagnetic radiation having a wavelength within an absorption band of the sample,
   partially-reflective means for partially reflecting said electromagnetic radiation at successive positions which are spaced apart from each other along a predetermined path along a single geometrical ray through the sample, said partially-reflective means being effective at each said successive position to separate incident radiation into a reflected part which is caused by the partially-reflective means to follow said predetermined path and an unreflected part,
   and derivation means for deriving a value of said decay from measurements of intensity of the unreflected parts of the electromagnetic radiation produced at a number of different said positions along said predetermined path.

2. An apparatus as claimed in claim 1 wherein said derivation means derives said value of decay from measurements of intensity of the unreflected parts of the electromagnetic radiation produced at all said positions along said predetermined path.

3. An apparatus as claimed in claim 1 wherein said partially-reflective means comprises a plurality of discrete partially-reflective elements.

4. An apparatus as claimed in claim 1 wherein said partially-reflective means comprises at least one partially-reflective element, the or each said partially-reflective element being arranged to partially reflect said electromagnetic radiation incident at a plurality of said positions.

5. An apparatus as claimed in claim 4 wherein said partially-reflective means comprises a pair of parallel, partially-reflective plates arranged so that said predetermined path extends alternately between the plates.

6. An apparatus as claimed in claim 5 wherein said source is arranged to direct a beam of electromagnetic radiation onto a surface of one of said plates at an angle to said surface no greater than 10°.

7. An apparatus as claimed in claim 1 wherein said partially reflective means is so arranged that said predetermined path occupies a substantially two-dimensional plane.

8. An apparatus as claimed in claim 1 wherein said partially-reflective means is so arranged that said predetermined path occupies a three-dimensional space.

9. An apparatus as claimed in claim 1 including a chamber for containing said sample.

10. An apparatus as claimed in claim 9 including means for admitting sample to and discharging sample from, the chamber.

11. An apparatus as claimed in claim 9 wherein said partially-reflective means is supported by or formed in a wall of the chamber.

12. An apparatus as claimed in claim 9 wherein said source is external to said chamber.

13. An apparatus as claimed in claim 9 wherein said source is internal to said chamber.

14. An apparatus as claimed in claim 9 wherein said source forms part of the chamber wall.

15. An apparatus as claimed in claim 1 wherein said partially-reflective means has substantially the same reflection coefficient at each said successive position.

16. An apparatus as claimed in claim 1 wherein said source of electromagnetic radiation is a pulsed source.

17. An apparatus as claimed in claim 1 wherein said source of electromagnetic radiation is a monochromatic source.

18. An apparatus as claimed in claim 1 wherein said source of electromagnetic radiation is a wideband source.

19. An apparatus as claimed in claim 1 wherein said source simultaneously produces electromagnetic radiation at a number of discrete wavelengths.

20. An apparatus as claimed in claim 1 wherein said source of electromagnetic radiation produces electromagnetic radiation in the wavelength range from 2 nm to 10 mm.

21. An apparatus as claimed in claim 1 wherein said different positions are spaced apart from each other equidistantly.

22. A method for measuring decay in intensity of electromagnetic radiation passing through a radiation-absorbent sample due to absorption of radiation by the sample, comprising,
    generating electromagnetic radiation having a wavelength within an absorption band of the sample,
    partially-reflecting said electromagnetic radiation at successive positions which is spaced apart from each other along a predetermined path along a single geometrical ray through the sample, whereby to separate radiation into a reflected part which is caused to follow said predetermined path and an unreflected part,
    and deriving a value of said decay from measurements of intensity of the unreflected parts of the electromagnetic radiation produced at a number of different said positions along said predetermined path.

* * * * *